(12) United States Patent
Tabaru et al.

(10) Patent No.: US 8,850,870 B2
(45) Date of Patent: Oct. 7, 2014

(54) PRESSURE GUIDING TUBE BLOCKAGE DIAGNOSING DEVICE AND BLOCKAGE DIAGNOSING METHOD

(75) Inventors: Tetsuya Tabaru, Tokyo (JP); Masato Tanaka, Tokyo (JP)

(73) Assignee: Azbil Corporation, Tokyo (JP)

( * ) Notice: Subject to any disclaimer, the term of this patent is extended or adjusted under 35 U.S.C. 154(b) by 494 days.

(21) Appl. No.: 13/132,120

(22) PCT Filed: Dec. 1, 2009

(86) PCT No.: PCT/JP2009/070173
§ 371 (c)(1),
(2), (4) Date: Jun. 1, 2011

(87) PCT Pub. No.: WO2010/064629
PCT Pub. Date: Jun. 10, 2010

(65) Prior Publication Data
US 2011/0232369 A1    Sep. 29, 2011

(30) Foreign Application Priority Data
Dec. 1, 2008   (JP) .................................. 2008-306288

(51) Int. Cl.
*G01M 3/02* (2006.01)
*G01L 27/00* (2006.01)
*G01N 3/32* (2006.01)

(52) U.S. Cl.
CPC ................ *G01L 27/007* (2013.01); *G01N 3/32* (2013.01)
USPC .............................................................. 73/37

(58) Field of Classification Search
CPC ....................................................... G01N 3/32
USPC .............................................................. 73/37
See application file for complete search history.

(56) References Cited

U.S. PATENT DOCUMENTS

| 3,994,166 A | 11/1976 | Dower |
| 5,663,509 A | 9/1997 | Lew et al. |
| 6,571,124 B1 | 5/2003 | Storm |

(Continued)

FOREIGN PATENT DOCUMENTS

| CN | 1898535 A | 1/2007 |
| JP | 7-11473 B2 | 2/1995 |

(Continued)

OTHER PUBLICATIONS

Japanese Office Action dated Aug. 31, 2012, which issued in Japanese Patent Application No. 2008-306288.

(Continued)

*Primary Examiner* — Hezron E Williams
*Assistant Examiner* — Rodney T Frank
(74) *Attorney, Agent, or Firm* — Troutman Sanders LLP

(57) ABSTRACT

A pressure transmitting device detects, through a pressure guiding tube, a pressure of a liquid, slurry, gas, or the like to be measured, wherein there are fluctuations in the pressure; where the pressure guiding tube blockage diagnosing device comprises: a rising/falling frequency detecting portion for segmenting into a plurality of continuous intervals a time series of pressure values detected by the pressure transmitting device, and for detecting, in each time interval, the rising/falling frequency of the fluctuations; and an evaluating portion for evaluating the state of blockage of the pressure guiding tube through comparing, to a specific threshold value, the rising/falling frequency of the fluctuations.

14 Claims, 15 Drawing Sheets

(56) References Cited

U.S. PATENT DOCUMENTS

| | | |
|---|---|---|
| 6,904,810 B2 | 6/2005 | Oomura et al. |
| 7,406,387 B2 | 7/2008 | Hashizume et al. |
| 7,523,667 B2 | 4/2009 | Brown et al. |
| 2007/0079180 A1 | 4/2007 | Miyamoto |
| 2011/0232369 A1 | 9/2011 | Tabaru et al. |
| 2011/0308299 A1* | 12/2011 | Tabaru .............................. 73/37 |

FOREIGN PATENT DOCUMENTS

| | | |
|---|---|---|
| JP | 7-294356 A | 11/1995 |
| JP | 8-136386 A | 5/1996 |
| JP | 2000-3194 A | 1/2000 |
| JP | 2000-55950 A | 2/2000 |
| JP | 2000-291337 A | 10/2000 |
| JP | 2002-5772 A | 1/2002 |
| JP | 2002-162307 A | 6/2002 |
| JP | 2003500149 A | 1/2003 |
| JP | 2007-85933 A | 4/2007 |
| JP | 2007-256231 A | 10/2007 |
| JP | 2008-306288 A | 12/2008 |
| JP | 2009-085769 A | 4/2009 |
| WO | 00/72751 A1 | 12/2000 |

OTHER PUBLICATIONS

Chinese Office Action dated Aug. 24, 2012, which issued in Chinese Patent Application No. 200980147888.9.

* cited by examiner

PRESSURE GUIDING TUBE BLOCKAGE DIAGNOSING DEVICE AND BLOCKAGE DIAGNOSING METHOD

CROSS REFERENCE TO PRIOR APPLICATIONS

This application is a U.S. National Phase application under 35 U.S.C. §371 of International Application No. PCT/JP2009/070173, filed on Dec. 1, 2009 and claims benefit of priority to Japanese Patent Application No. 2008-306288, filed on Dec. 1, 2008. The international Application was published in Japanese on Jun. 10, 2010 as WO 2010/064629 A1 under PCI Article 21(2). All these applications are herein incorporated by reference.

FIELD OF TECHNOLOGY

The present invention relates to a pressure measuring device for measuring pressure to be measured through the introduction, into a pressure transmitting device through a pressure guiding tube, a liquid, a slurry, a gas, or the like, to be measured, wherein there are fluctuations in pressure, and in particular, relates to a blockage diagnosing device and blockage diagnosing method for diagnosing a state of blockage of the pressure guiding tube.

BACKGROUND OF THE INVENTION

Conventionally, in the process industry field, pressure transmitting devices have been used in order to control processes by detecting, for example, the amounts of variations in processes. Pressure transmitting devices are also known as pressure sending devices. These pressure transmitting devices are able to measure amounts of process variations, such as in pressure, flow rates, fluid levels, specific gravities, and the like, through measuring differential or absolute pressures between two points. Typically, when measuring the amounts of process variations using pressure transmitting devices, that which is to be measured is introduced into the pressure transmitting device through a thin tube, known as a pressure guiding tube, from, for example, both sides of a differential pressure generating mechanism, such as an orifice, that is disposed in a process pipe wherein that which is to be measured, such as a liquid, is flowing.

In this type of device structure, blockages in the pressure guiding tubes may result from the adherence, to the interior of the pressure guiding tubes, of solid objects, or the like, according to that which is being measured. If a pressure guiding tube becomes completely blocked, then it becomes impossible to measure the process variations accurately, which can have a serious impact on the plant. However, because pressure is still transmitted to the pressure transmitting device up until the point wherein the pressure guiding tube becomes completely blocked, the impact of the blockage tends to not appear in the process variation measurement values. Remote seal-type pressure transmitting devices wherein pressure guiding tubes are not required have been developed in response to this type of problem. However, an extremely large number of plants measure process variations using pressure guiding tubes, and thus there is the need to be able to perform pressure guiding tube blockage diagnostic functions on-line.

Conventionally, the technologies disclosed in Japanese Examined Patent Application Publication H7-11473 and Japanese Patent 3139597 have been known as technologies for diagnosing the state of pressure guiding tube blockage. The fault detecting device disclosed in Japanese Examined Patent Application Publication H7-11473, as illustrated in FIG. 20, inputs, over a specific time interval, a signal regarding that which is being measured, detects the maximum amplitude W of variation in the inputted signal within a given time interval, and compares the detected maximum variation amplitude W to a threshold value that has been set in advance, to determine that there is a fault in the signal if the maximum variation amplitude W is smaller then the threshold value. In FIG. 20, Smax is the maximum value for the signal, and Smin is the minimum value for the signal. Japanese Examined Patent Application Publication H7-11473 discloses that pressure guiding tube blockage status diagnosis can be performed through the application of this fault detecting device.

In the fault detecting device disclosed in Japanese Examined Patent Application Publication H7-11473, if the set time period that is interval for detecting the maximum variation of the signal is sufficiently much longer than the period of the variation of the signal, then the effect will be to detect a maximum variation amplitude W from among the difference between adjacent maximum values and minimum values. Additionally, if the aforementioned set time period is shorter than the period of the variation of the signal, then the effect will be to detect the maximum variation amplitude W simply within the set time period. In particular, if the signal is sampled discontinuously, the aforementioned set time period is set so as to detect amount of variation in a single sampling interval, then the effect will be to detect a difference value (that is, the differential value) of the signal.

The blockage diagnosing device disclosed in Japanese Patent 3139597 detects the fluctuation (variation) in pressure of that which is being measured, and evaluates that a blockage has occurred in the pressure guiding tube when the difference between the detected magnitude of fluctuation and the magnitude of normal fluctuation exceeds a value that has been set in advance. In Japanese Patent 3139597, a pressure differential signal and a difference signal between an upper peak (the maximum value) and a lower peak (a minimum value) for pressure are given as examples of signals indicating fluctuations in pressure. The signal for the differential in the pressure, disclosed in Japanese Patent 3139597, corresponds to the difference value of the signal disclosed in Japanese Examined Patent Application Publication H7-11473, and the difference signal disclosed in Japanese Patent 3139597 corresponds to the maximum variation amplitude W disclosed in Japanese Examined Patent Application Publication H7-11473. Consequently, the technology disclosed in Japanese Examined Patent Application Publication H7-11473 and the technology disclosed in Japanese Patent 3139597 can be said to be based on the same technical concept.

As described above, in the technology disclosed in Japanese Examined Patent Application Publication H7-11473 and Japanese Patent 3139597, the state of blockage of a pressure guiding tube is diagnosed based on the magnitude of the fluctuation in pressure, a threshold value to serve as a reference in the diagnosis is required and at the time of the diagnosis. In the technology disclosed in Japanese Examined Patent Application Publication H7-11473 and Japanese Patent 3139597, there is a problem in that this threshold value must be adjusted appropriately in accordance to the magnitude of the pressure, and a problem in that time and specialized knowledge is required to adjust the threshold value.

For ease in understanding, the conventional problem areas will be explained assuming extreme numerical values. For example, even if a fluctuation of ±3 kPa is normal in a pressure value of 100 kPa, a fluctuation of ±3 kPa could not be considered normal in a pressure value of 5 kPa. Consequently, it would be inappropriate to use the same threshold value when the pressure value is 100 kPa as when the pressure value is 5 kPa, and the threshold value must be made smaller for the case of the pressure value of 5 kPa.

Additionally, one cannot diagnose the same state of blockage in a case of a 2 kPa fluctuation instantaneously from a pressure of 80 kPa to 82 kPa, in a state wherein, for example, the pressure would be about 100 kPa if smoothing were performed, as in a case of a 2 kPa fluctuation instantaneously from a pressure of 80 kPa to 82 kPa, in a state wherein the pressure would be about 60 kPa if smoothing were performed. Consequently, the same threshold values would not be considered to be appropriate in both of these cases.

As is clear from the explanation above, in the technologies disclosed in Japanese Examined Patent Application Publication H7-11473 and Japanese Patent 3139597, it is necessary to adjust the threshold value that is the reference for the diagnosis.

The present invention is to solve the problem areas set forth above, and the object thereof is to provide a pressure guiding tube blockage diagnosing device and blockage diagnosing method able to reduce the need to change the threshold value that is the reference for the diagnosis.

SUMMARY OF THE INVENTION

A pressure guiding tube blockage diagnosing device according to the present invention includes a pressure detector for detecting, through a pressure guiding tube, a pressure that is to be measured, having a fluctuation in the pressure; fluctuation speed detector for detecting a speed of a fluctuation, based on pressure values detected by the pressure detector; and evaluator for evaluating a state of blockage of a pressure guiding tube based on the speed of fluctuation.

A pressure guiding tube blockage diagnosing method according to the present invention has a pressure detecting step for detecting, through a pressure guiding tube, a pressure that is to be measured, having a fluctuation in the pressure; a fluctuation speed detecting step for detecting a speed of a fluctuation, based on pressure values detected by the pressure detecting step; and an evaluating step for evaluating a state of blockage of a pressure guiding tube based on the speed of fluctuation.

The present invention enables a reduction in the need to adjust the threshold value, by detecting the speed of fluctuation of the pressure and evaluating the state of blockage of the pressure guiding tube based on the speed of fluctuation, to eliminate the need to make fine changes to the threshold values that serve as the references for the diagnosis.

DETAILED DESCRIPTION OF THE INVENTION

Because the pressure fluctuation phenomenon is a dynamic phenomenon, it is possible to detect information corresponding to the amplitude and frequency of the fluctuation. Conceptually, the technologies disclosed in Japanese Examined Patent Application Publication H7-11473 and Japanese Patent 3139597 detect the amplitude of fluctuations.

As the result of investigations into the phenomenon of pressure guiding tube blockages, the inventors focused on the ability to diagnose, conceptually, the state of blockage of the pressure guiding tube through the method of detecting the frequency of fluctuations (speed of fluctuations) in the pressure, so arrived at the use of a method of counting the rising/falling frequency of the fluctuations within a specific time interval as a method for detecting easily information corresponding to the speed of the fluctuations. When counting the rising/falling frequency of the fluctuations within a specific time interval, preferably noise, which has a frequency that is higher than the primary component of the pressure fluctuation, is eliminated.

Because the state of the amplitude of the fluctuation varies linked to the scope of change in the pressure value itself when diagnosing the state of blockage of the pressure guiding tube by detecting the amplitude of the fluctuation of the pressure using the technologies disclosed in Japanese Examined Patent Application Publication H7-11473 and Japanese Patent 3139597, it is necessary to vary, in accordance with this change, the threshold value that is the reference for the diagnosis.

On the other hand, when diagnosing the state of blockage of the pressure guiding tube by detecting the rising/falling frequency of the fluctuation in the pressure, as in the present invention, the rising/falling frequency of the fluctuation will vary with, for example, the viscosity of the fluid that is being measured, and if the pressure guiding tube is operating properly there will be no large changes in the rising/falling frequency as long as there is no change in, for example, the viscosity of that which is being measured, and thus the change in the status will remain within an extremely limited range. Consequently, it is unlikely that there will be the same problems as in the technologies disclosed in Japanese Examined Patent Application Publication H7-11473 and Japanese Patent 3139597. That is, the present invention enables a reduction in the need to change the threshold value.

Figure 1:
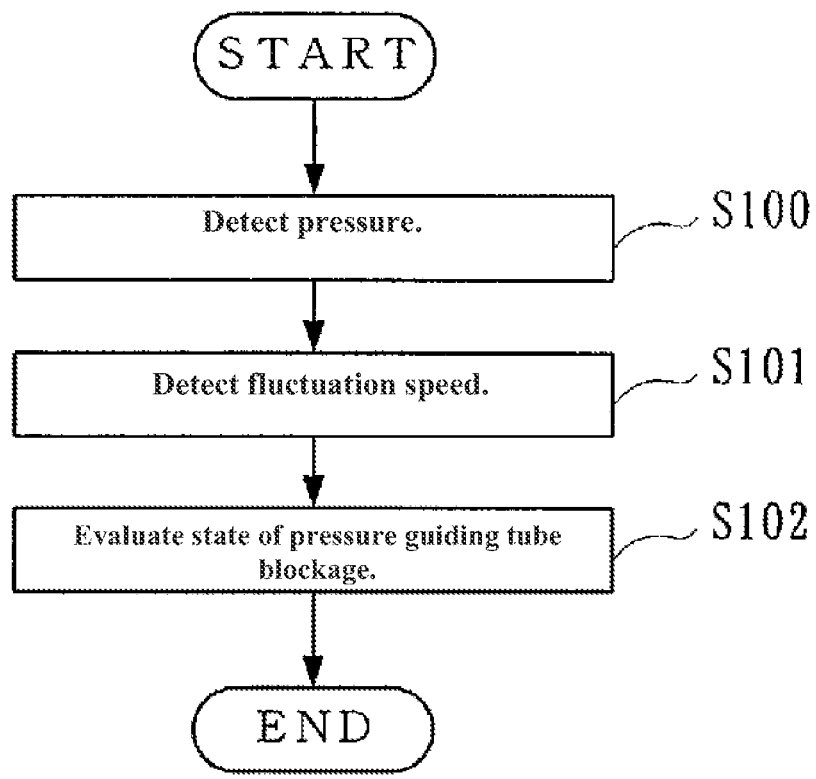
FIG. 1 is a flowchart for explaining the pressure guiding tube blockage diagnosing method according to the present invention.

FIG. 1 is a flowchart for explaining the pressure guiding tube lockets diagnosing method according to the present invention. In the present invention, the pressure to be measured, wherein there are fluctuations in the pressure, is detected through a pressure guiding tube (Step S100), the speed of the fluctuations is detected based on the detected pressure values (Step S101), and the state of blockage of the pressure guiding tube is diagnosed based on the speed of the fluctuations (Step S102).

Figure 2:
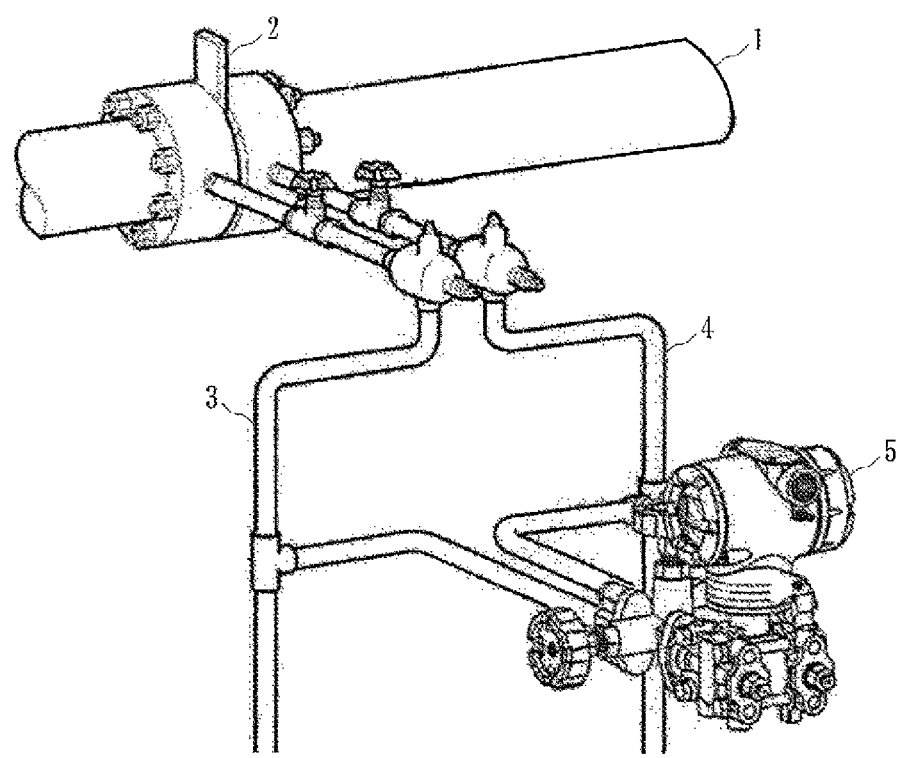
FIG. 2 is a perspective view illustrating the structure of a pressure measuring device according to the first example of embodiment according to the present invention.

An example according to the present invention is explained next. FIG. 2 is a perspective view illustrating the structure of a pressure measuring device according to the example. A pipe 1 is a conduit wherein flows that which is to be measured, such as a liquid, a slurry, or a gas; 2 is an orifice that is a pressure generating mechanism disposed in the pipe 1; 3 and 4 are pressure guiding tubes; and 5 is a pressure transmitting device that is the pressure detector.

The pressure guiding tubes 3 and 4 guide that which is to be measured to the pressure transmitting device 5, from two points on both sides of the orifice 2. The pressure transmitting device 5 measures the differential pressure of that which is to be measured at the two points, and measures the pressure of that which is to be measured, in reference to either vacuum or atmospheric pressure. In the present example, the pressure transmitting device 5 measures the pressure of that which is to be measured, in reference to either vacuum or atmospheric pressure. The pressure transmitting device 5 outputs an electric signal indicating the measured pressure value.

Figure 3:
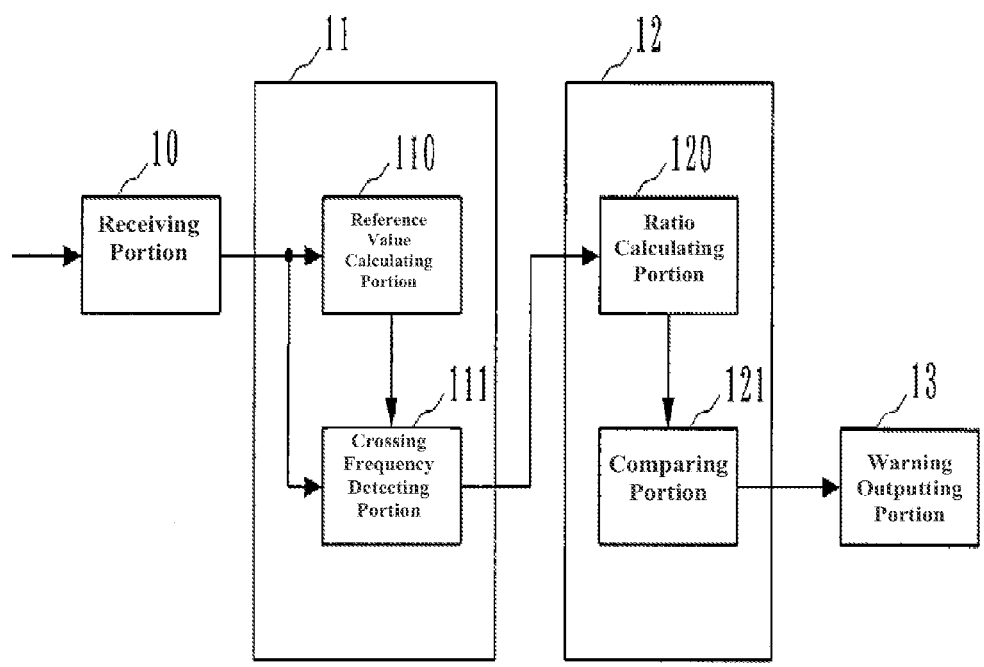
FIG. 3 is a block diagram illustrating the structure of a pressure guiding tube blockage diagnosing device according to an example of the present invention.

FIG. 3 is a block diagram illustrating the structure of a pressure guiding tube blockage diagnosing device according to an example of the present invention. The blockage diagnosing device is structured from a receiving portion 10 for receiving a signal outputted from the pressure transmitting device 5; a rising/falling frequency detecting portion 11 as fluctuation speed detector for detecting the speed of fluctuation of the pressure based on the pressure values measured by the pressure transmitting device 5; an evaluating portion 12 for evaluating the state of blockage of the pressure guiding tubes 3 and 4 based on the rising/falling frequency of the fluctuation; and a warning outputting portion 13 for issuing a warning when there is an evaluation that a blockage has occurred in the pressure guiding tube 3 and/or 4.

The rising/falling frequency detecting portion 11 includes a reference value calculating portion 110 and a crossing frequency detecting portion 111. The evaluating portion 12 has a ratio calculating portion 120 and a comparing portion 121.

Figure 4:
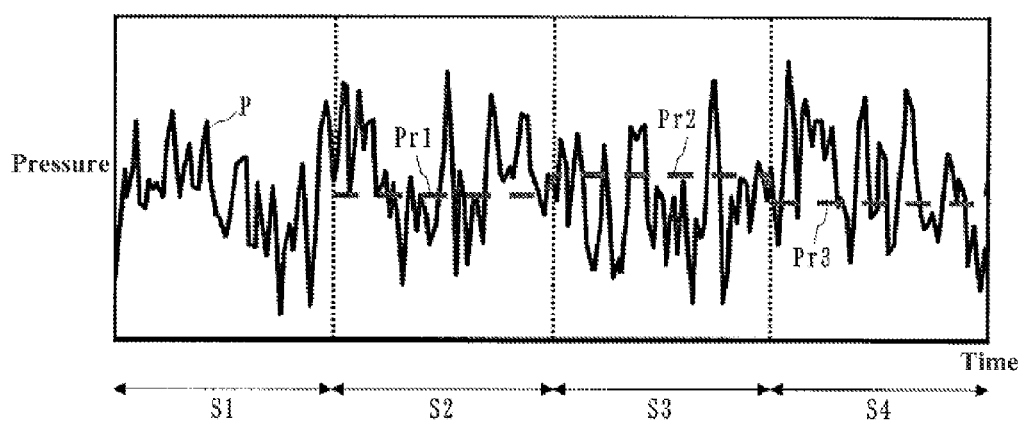
FIG. 4 is a waveform diagram for explaining the operation of a pressure guiding tube blockage diagnosing device according to an example of the present invention.

The operation of the blockage diagnosing device according to the present example is explained next. FIG. 4 is a waveform diagram for explaining the operation of the blockage diagnosing device according to the present example, a diagram illustrating one example of the changes in the pressure value P measured by the pressure transmitting device 5. Note that while in FIG. 4 the waveform is illustrated as the pressure values P being connected, the signal that is actually processed in the present example of embodiment is pressure data that are sampled periodically.

The receiving portion 110 receives pressure data outputted from the digital output terminals of the pressure transmitting device 5. Note that, of course, form may be one wherein the pressure transmitting device 5 outputs an analog signal, and the receiving portion 10 performs A/D conversion on the analog signal that is outputted from the pressure transmitting device 5, to output the pressure data.

The reference value calculating portion 110 of the rising/falling frequency detecting portion 11, as illustrated in FIG. 4, segments the time series of the pressure values P into a plurality of connected continuous intervals S1, S2, S3, S4, . . . , and calculates, for each interval, the reference value Pr of the pressure value P. Pr1, Pr2, and Pr3, illustrated in FIG. 4, are the respective reference values calculated in intervals S1, S2, and S3. The intervals may be segmented to have constant time intervals, or may be segmented to have a constant number of samples. Additionally, as reference values, there are the average values and the central values for the pressure value P for the applicable reference value calculating intervals.

Following this, the crossing frequency detecting portion 111 of the rising/failing frequency detecting portion 11 counts, for each interval, the number of times that the reference value Pr that was calculated during the immediately previous interval is crossed by the pressure value P during the applicable detection interval. That is, if the applicable detection interval is S2, then the number of times that the pressure value P in the interval S2 crosses the reference value Pr1, which was calculated during the immediately previous interval S1, is counted. The crossing frequency is the pressure fluctuation rising/falling frequency.

Following this, the ratio calculating portion 120 of the evaluating portion 12 calculates, for each interval, the ratio of the crossing frequency, counted by the crossing frequency detecting portion 111, divided by the number of samples in the interval, in order to normalize the detecting results by the crossing frequency detecting portion 111.

The comparing portion 121 of the evaluating portion 12 compares the ratio calculated by the ratio calculating portion 120 to a threshold value that has been set in advance, and if the ratio is continuously lower than the threshold value, then the evaluation is that a blockage has occurred in the pressure guiding tubes 3 and 4. Specifically, when the ratio is less than the threshold value a specific number of times in a row, or if the average value for the ratio for a specific number of intervals is less than the threshold value, then the comparing portion 121 may determine that a blockage has occurred in the pressure guiding tube 3 or the pressure guiding tube 4.

The warning outputting portion 12 outputs a warning if the evaluation is that a blockage has occurred in the pressure guiding tube 3 or 4. The warning notification at this may be, for example, an audible notification such as a buzzer, or a notification by illuminating a lamp.

Figure 5:
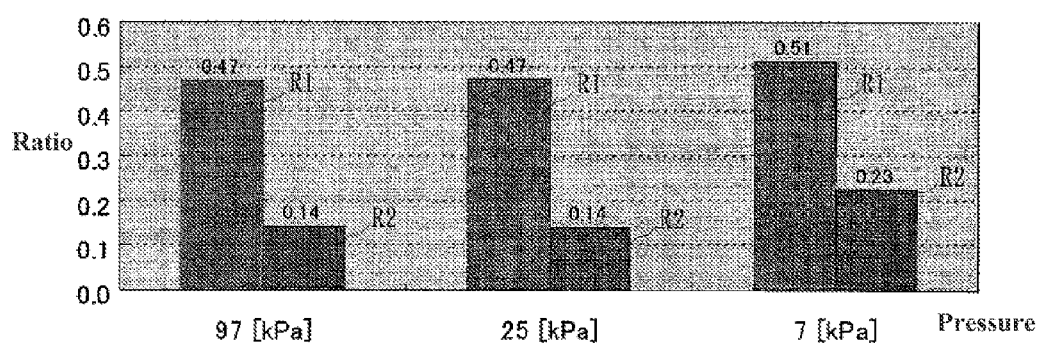
FIG. 5 is a diagram for explaining the effects of a pressure guiding tube blockage diagnosing device according to an example according to the present invention.

FIG. 5 is a diagram for explaining the effect of the present example of embodiment, a diagram illustrating the ratio of the crossing frequency to the number of samples in three pressure states. FIG. 5 is based on the data wherein the pressure was actually measured using a pressure measuring device as illustrated in FIG. 2. R1 in FIG. 5 is the ratio at the time of proper operation, and R2 is the ratio at the time of a fault when the pressure guiding tube is blocked. The pressure values, 97 kPa, 25 kPa, and 7 kPa, are values wherein pressure data from a plurality of intervals have been smoothed. The blockage of the pressure guiding tube was simulated by constricting the degree of opening of a three-way manifold valve attached to the pressure transmitting device 5. While there is some dependency on the number of samples during the interval, there is variability in the crossing frequency, and thus by summing and averaging the crossing frequencies for a plurality of intervals, the ratios were calculated by dividing the average values by a number that is one less than the number of samples in a single interval. The ratios assumed values between 0 and 1, and the value approached 0 the worst the blockage of the pressure guiding tube. The pressure data subject to measurement were obtained by measuring a differential pressure relative to atmosphere by opening to atmosphere either the high pressure side or the tow pressure side of the pressure transmitting device 5. While this produces an offset equal to the atmospheric pressure, this does not present an impediment to the investigations of the suitability of the present example.

It can be understood from FIG. 5 that the ratio is different during the proper operations and during the improper operations, and that the difference is adequate for diagnosing a pressure guiding tube blockage. In the example in FIG. 5, it can be seen that setting the threshold value to about 0.4 or 0.3 makes it possible to discriminate between the case wherein the pressure guiding tube is normal and the case wherein the pressure guiding tube is blocked. Moreover, it can be seen that there is no large change in the state of the ratio regardless of whether the pressure being measured is 97 kPa, 25 kPa, or 7 kPa, and thus there is no need to change the threshold value even if there is a large change in the pressure being measured.

As described above, the present example makes it possible to diagnose the state of blockage of the pressure guiding tube based on the rising/falling frequency of the fluctuation in pressure. In the present example, it is possible to reduce the need to adjust the threshold value, because it is not necessary to make fine adjustments to the threshold value that is used as the reference for the diagnosis. Additionally, in the present example the crossing frequency can be counted in real time, thus enabling application on-line to diagnosing the states of blockages of pressure guiding tubes when the processes are in the operating state.

Figure 6:
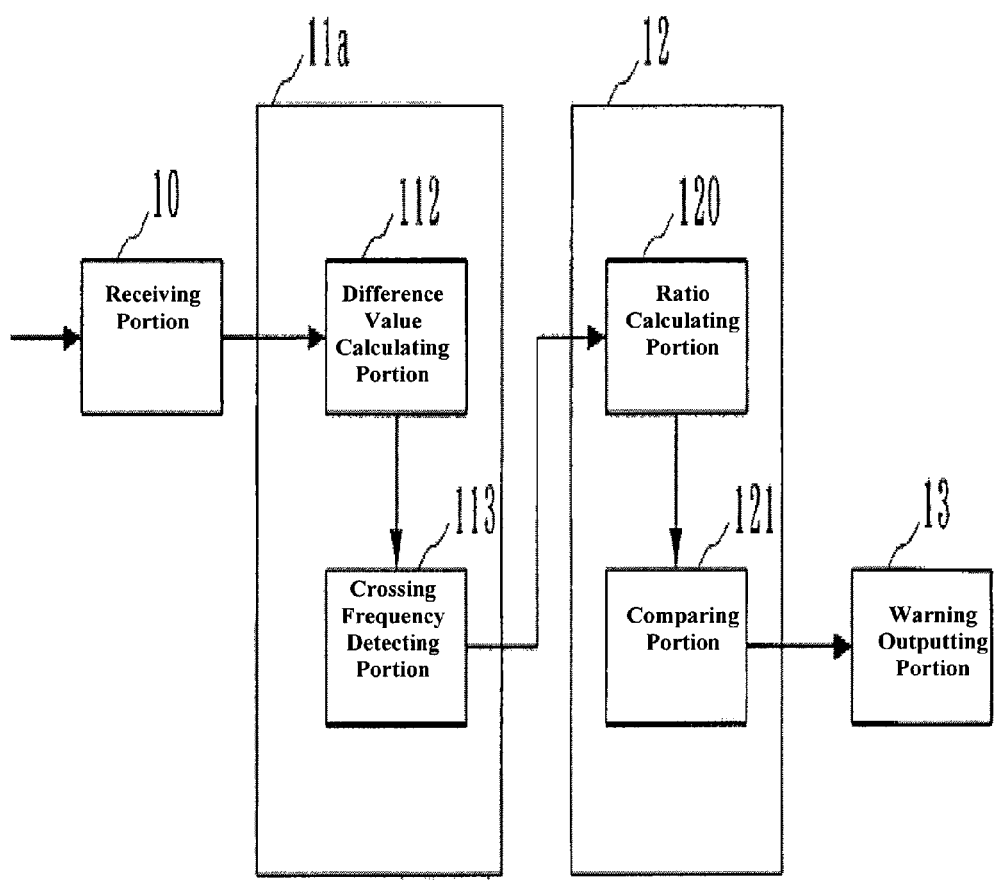
FIG. 6 is a block diagram illustrating the structure of a pressure guiding tube blockage diagnosing device according to another example according to the present invention.

Another example of the present invention is explained next. FIG. 6 is a block diagram illustrating the structure of a pressure guiding tube blockage diagnosing device according to an example of embodiment according to the present invention, where structures identical to those in FIG. 3 are assigned identical codes. The blockage diagnosing device according to the present example is structured from a receiving portion 10; a rising/falling frequency detecting portion 11a; an evaluating portion 12; and a warning outputting portion 13.

In the present example, the frequency of switching between rising and falling in the pressure fluctuation is counted as the rising/falling frequency. The rising/falling frequency detecting portion 11a comprises a difference value calculating portion 112 and a crossing frequency detecting portion 113.

The operation of the blockage diagnosing device according to the present example is explained next. The difference value calculating portion 112 of the rising/falling frequency detecting portion 11a divides the time series of the pressure values P into a plurality of continuous intervals and calculates a difference value Pd (t) as a difference between the pressure value P (t) and the pressure value P (t−d) from a specific time interval earlier, as in the equation below:

$$Pd(t)=P(t)-P(t-d) \quad (1)$$

If the sampling period is selected as the specific time interval d, then this will be the difference from the immediately previous sample value, and will be equivalent to calculating the first-order differences in pressure values. However, the set time interval d need not be the sampling period. The difference value calculating portion 112 performs calculations such as described above with each pressure sample value.

The crossing frequency detecting portion 113 of the rising/falling frequency detecting portion 11a counts, for each interval, the number of times the difference value calculated by the difference value calculating portion 112 crosses zero (the number of zero crossings). The number of zero crossings serves as the rising/falling frequency for the fluctuation of the pressure.

As with the above example, the ratio calculating portion 120 of the evaluating portion 12 calculates, for each interval, a ratio wherein the number of zero crossings, counted by the crossing frequency detecting portion 113, is divided by the number of samples in an interval. The operation of the comparing portion 121 and the warning outputting portion 13 are identical to those in the example above.

Figure 7:
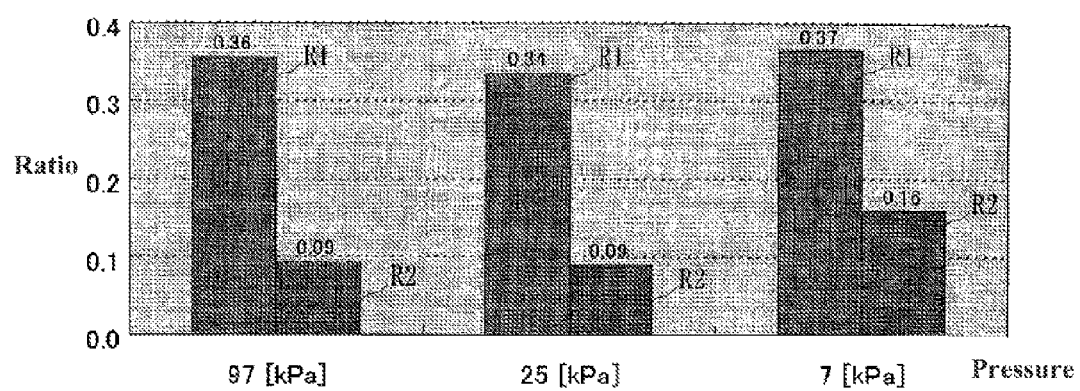
FIG. 7 is a diagram for explaining the effects of a pressure guiding tube blockage diagnosing device according to another example according to the present invention.

FIG. 7 is a diagram for explaining the effect of the present example, a diagram illustrating the ratio of the zero crossing frequency to the number of samples in three pressure states. FIG. 7 is based on pressure data calculated in the same manner as in the case in FIG. 5. It can be understood from FIG. 7 that the ratio is different during the proper operations and during the improper operations, and that the difference is adequate for diagnosing a pressure guiding tube blockage. In the example in FIG. 7, it can be seen that setting the threshold value to about 0.3 or 0.2 makes it possible to discriminate between the case wherein the pressure guiding tube is normal and the case wherein the pressure guiding tube is blocked. Moreover, it can be seen that there is no large change in the state of the ratio regardless of whether the pressure being measured is 97 kPa, 25 kPa, or 7 kPa, and thus there is no need to change the threshold value even if there is a large change in the pressure being measured.

As described above, the same effect as in the above example can be obtained through the present example. In the present example, the pressure value is subjected to a high pass filter process, making it possible to extract only the fluctuations in pressure.

Note that a difference in differences between pressure values may instead be calculated in the difference value calculating portion 112. In such a case, the pressure value is subjected to a stronger high pass filter process, making it possible to emphasize the extraction of only the fluctuations in pressure.

Figure 8:
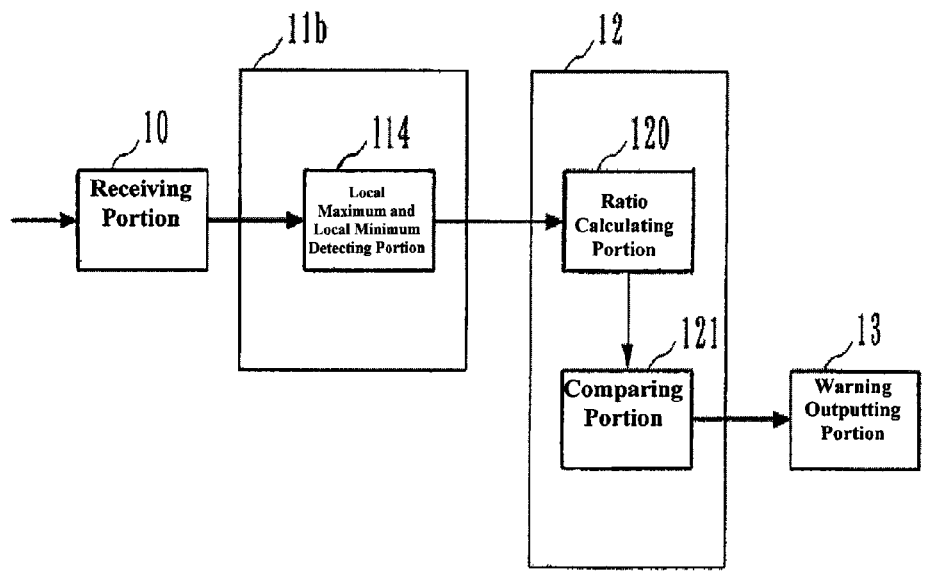
FIG. 8 is a block diagram illustrating the structure of a pressure guiding tube blockage diagnosing device according to a further example according to the present invention.

A further example of the present invention is explained next. FIG. 8 is a block diagram illustrating the structure of a pressure guiding tube blockage diagnosing device according to a further example according to the present invention, where structures identical to those in FIG. 3 are assigned identical codes. The blockage diagnosing device according to the present example is structured from a receiving portion 10; a rising/falling frequency detecting portion 11b; an evaluating portion 12; and a warning outputting portion 13.

The present example is based on the same concept as in the above example, but instead of the zero crossing frequency of the difference values, the number of local maxima and local minima of the pressures are counted as the rising/falling frequency.

The rising/falling frequency detecting portion 11b includes a local maximum and local minimum detecting portion 114. The local maximum and local minimum detecting portion 114 segments the time series of the pressure values P into a plurality of continuous intervals, and counts the number of local maxima and local minima of the pressure values P for each interval.

As with the above examples, the ratio calculating portion 120 of the evaluating portion 12 calculates, for each interval, a ratio wherein the number of local maxima and local minima, counted by the local maximum and local minimum detecting portion 114, is divided by the number of samples in an interval. The operation of the comparing portion 121 and the warning outputting portion 13 are identical to those in the example above.

As described above, the same effect as in the above examples can be obtained through the present example.

Figure 9:
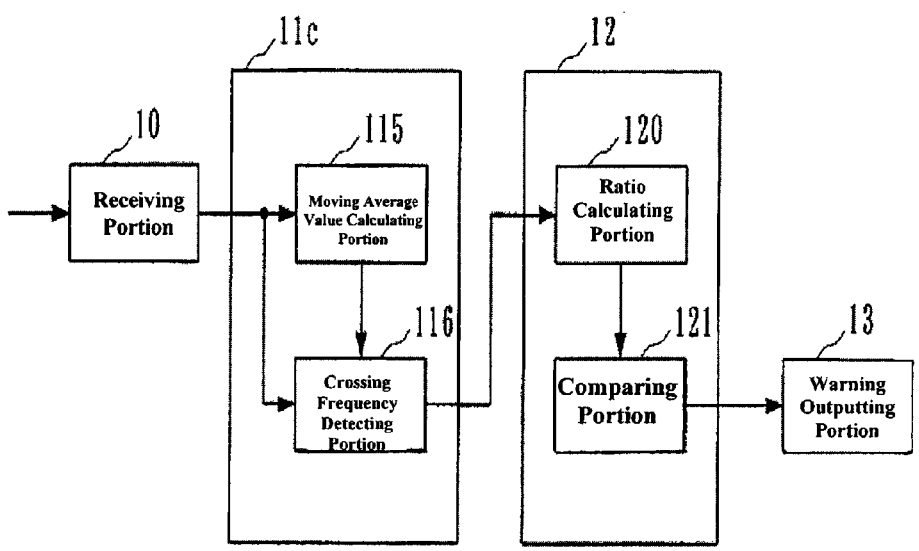
FIG. 9 is a block diagram illustrating the structure of a pressure guiding tube blockage diagnosing device according to yet another example according to the present invention.

Yet another example according to the present invention is explained next. FIG. 9 is a block diagram illustrating the structure of a pressure guiding tube blockage diagnosing device according to yet another example of the present invention, where structures identical to those in FIG. 4 are assigned identical codes. The blockage diagnosing device according to the present example is structured from a receiving portion 10; a rising/falling frequency detecting portion 11c; an evaluating portion 12; and a warning outputting portion 13.

The rising/falling frequency detecting portion 11c includes a moving average value calculating portion 115 and a crossing frequency detecting portion 116.

Figure 10A:
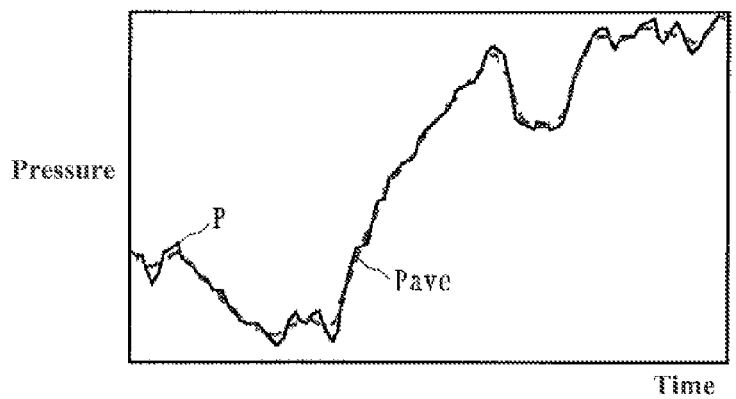
FIG. 10A-10B are waveform diagrams for explaining the operation of a pressure guiding tube blockage diagnosing device according to the yet another example.
Figure 10B:
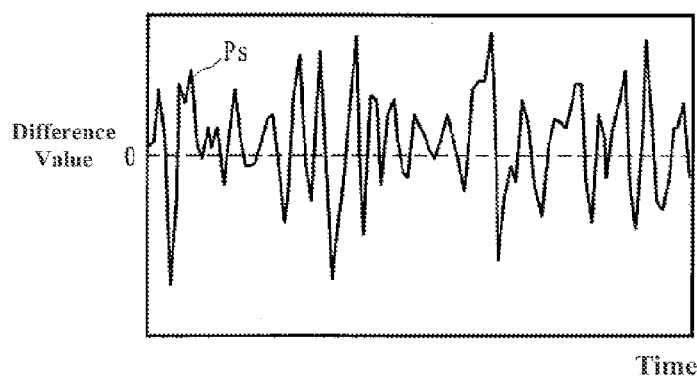

FIG. 10A and FIG. 10B are waveform diagrams for explaining the operation of the blockage diagnosing device according to the present example, where FIG. 10A is a diagram illustrating one example of the pressure values P measured by the pressure transmitting device 5 and the changes in the moving average values Pave thereof, and FIG. 10B is a diagram illustrating the difference values Ps between the pressure values P and the moving average values Pave. Note that while in FIG. 10A and FIG. 10B, the pressure values P, the moving average values Pave, and the difference values Ps are illustrated as continuous waveforms, in the present example the signals that are actually processed are pressure data that are sampled periodically, and the moving average values Pave and difference values Ps are also discrete data.

The moving average value calculating portion 115 segments the time series of the pressure values P into a plurality of continuous intervals, and calculates the moving average values Pave of the pressure values P. The moving average value Pave can use a normal moving average value, or a weighted moving average value, an exponentially weighted moving average (EWMA), which is a weighted moving average value having weightings that attenuate exponentially, calculated recursively. The moving average value calculating portion 115 performs calculations such as the moving average value Pave with each pressure sample value.

Following this, the crossing frequency detecting portion 116 counts, for each interval, the number of times that the pressure value P crosses the moving average value Pave in the applicable detection interval. Specifically, the crossing frequency detecting portion 116 may calculate the difference values Ps between the pressure values P and the moving average values Pave, as illustrated in FIG. 10B, to count, for each interval, the number of zero crossings of the difference values Ps. The number of zero crossings serves as the rising/falling frequency for the fluctuation of the pressure.

As with the examples above, the ratio calculating portion 120 of the evaluating portion 12 calculates, for each interval, a ratio wherein the number of zero crossings, counted by the crossing frequency detecting portion 116, is divided by the number of samples in an interval. The operation of the comparing portion 121 and the warning outputting portion 13 are identical to those in the above example.

Figure 11:
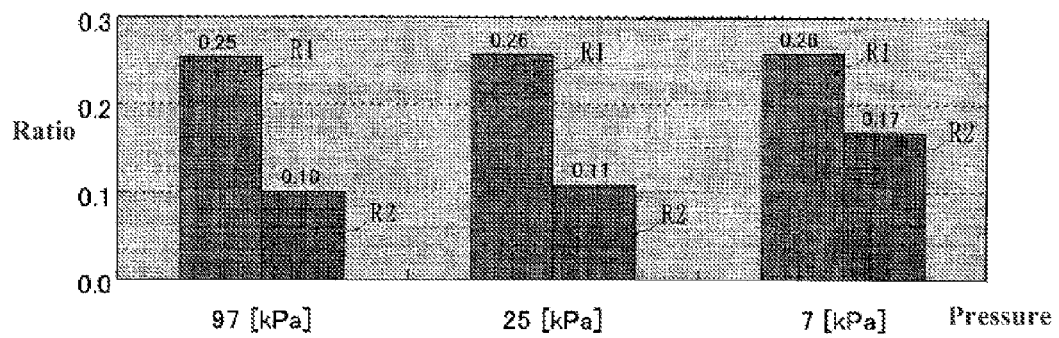
FIG. 11 is a diagram for explaining the effects of a pressure guiding tube blockage diagnosing device according to the yet another example according to the present invention.

FIG. 11 is a diagram for explaining the effect of the present example, a diagram illustrating the ratio of the zero crossing frequency to the number of samples in three pressure states. FIG. 11 is based on pressure data calculated in the same manner as in the case in FIG. 5. It can be understood from FIG. 11 that the ratio is different during the proper operations and during the improper operations, and that the difference is adequate for diagnosing a pressure guiding tube blockage. In the example in FIG. 11, it can be seen that setting the threshold value to about 0.2 makes it possible to discriminate between the case wherein the pressure guiding tube is normal and the case wherein the pressure guiding tube is blocked. Moreover, it can be seen that there is no large change in the state of the ratio regardless of whether the pressure being measured is 97 kPa, 25 kPa, or 7 kPa, and thus there is no need to change the threshold value even if there is a large change in the pressure being measured.

As described above, the same effect as in the above examples can be obtained through the present example. Additionally, in the present example, the calculations follow well the fluctuation in the pressure values P.

Figure 12:
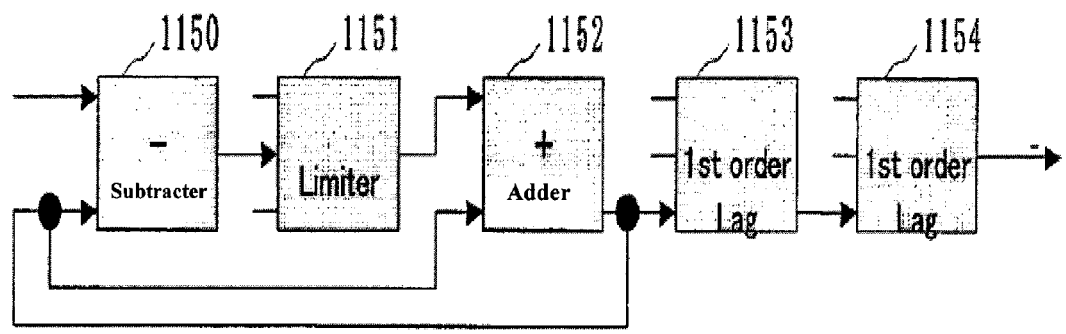
FIG. 12 is a block diagram illustrating an example of structure of a moving average calculating portion according to an example according to the present invention.

An example according to the present invention is explained next. FIG. 12 is a block diagram illustrating one configuration example of the moving average value calculating portion 115 illustrated in FIG. 9. The moving average value calculating portion 115 has a subtracting portion 1150, a limiter 1151, an adding portion 1152, and first-order lag processing portions 1153 and 1154.

Figure 13A:
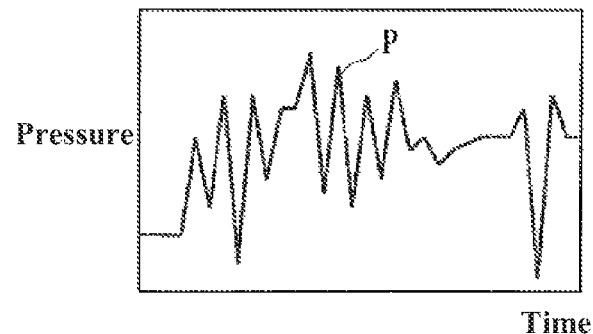
FIG. 13A-13C are waveform diagrams for explaining the operation of a moving average value calculating portion according to the example of the present invention.
Figure 13B:
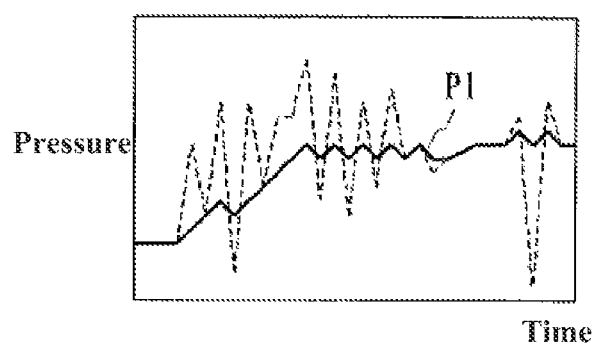
Figure 13C:
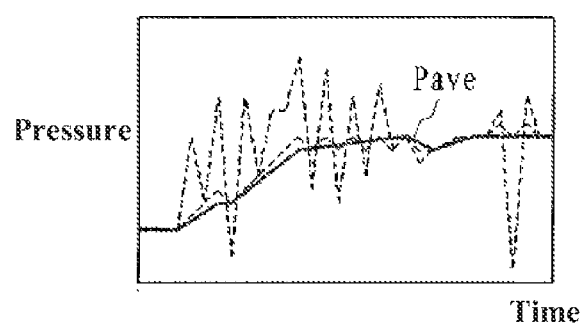

FIG. 13A, FIG. 13B, and FIG. 13C are waveform diagrams for explaining the operation of the moving average value calculating portion 115 in the present example, where FIG. 13A is a diagram illustrating one example of change in the pressure value P measured by the pressure transmitting device 5, FIG. 13B is a diagram illustrating a pressure value P1 after a change ratio limit process is performed on the pressure value and FIG. 13C is a diagram illustrating the pressure value Pave after a second-order lag process is performed on the pressure value P1. Note that while in FIG. 13A, FIG. 13B, and FIG. 13C the pressure values P, P1, and Pave are illustrated as continuous waveforms, in the present example the signals that are actually processed are pressure data that are sampled periodically, and pressure values P1 and Pave are also discrete data.

The subtracting portion 1150 subtracts, from the pressure value P, the previous value from one sample earlier. The limiter 1151 performs a limiting process to limit the difference value between the pressure value P and the previous value. The adding portion 1152 adds the output value of the limiter 1151 to the previous value from one sample earlier. Doing so causes the previous value, from one sample earlier, outputted from the adding portion 1152, to be a value wherein a change rate limit process has been performed, as in the pressure values P1 illustrated in FIG. 13B.

Following this, the first-order lag processing portion 1153 performs a first-order lag process on the pressure values P1 and the first-order lag processing portion 1154 performs a first-order lag process on the output values from the first-order lag processing portion 1153. Given this, the values outputted from the first-order lag processing portion 1154 are values wherein a second-order lag process has been performed, as in the pressure values Pave illustrated in FIG. 13C.

The present example enables smoothing of the variations in the low frequency components of the pressure, other than those of the fluctuation phenomenon, making it possible to obtain in essentially real time quantitative values that are adequately near to the moving average value Pave (essentially average values), as explained in the above example. Additionally, the second-order lag time constant can be adjusted to exclude also the effect of high-frequency signal noise in the pressure values P.

The structures and operations other than those of the moving average value calculating portion 115 are as explained in the example above.

Figure 14:
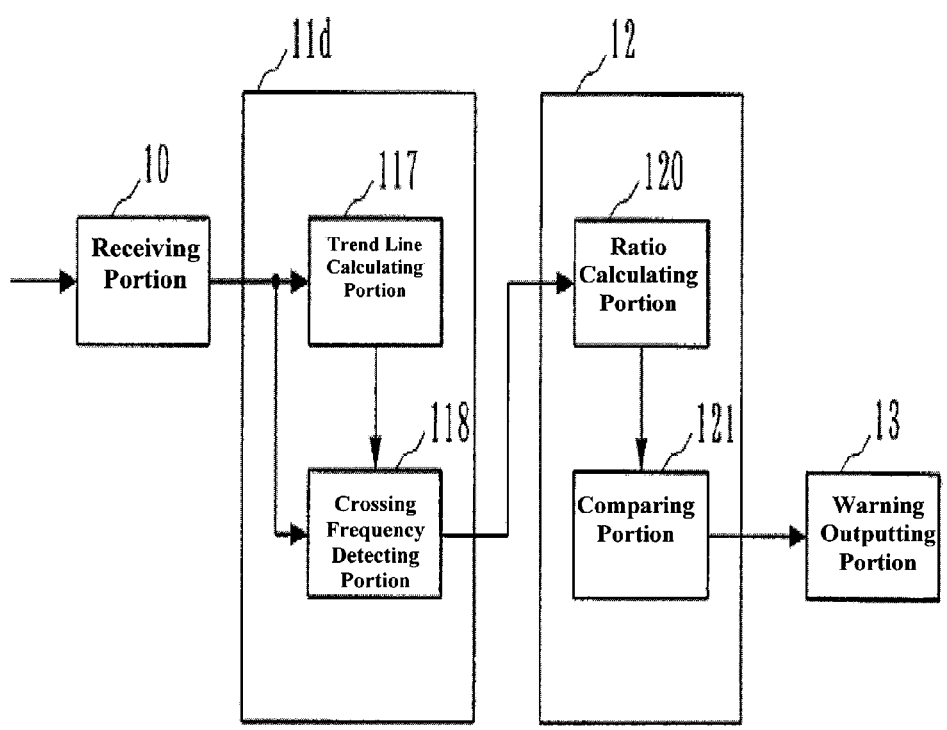
FIG. 14 is a block diagram illustrating the structure of a pressure guiding tube blockage diagnosing device according to another example of the present invention.

Another example of the present invention is explained next. FIG. 14 is a block diagram illustrating the structure of a pressure guiding tube blockage diagnosing device according to another example according to the present invention, where structures identical to those in FIG. 3 are assigned identical codes. The blockage diagnosing device according to the present example is structured from a receiving portion 10; a rising/falling frequency detecting portion 11$d$; an evaluating portion 12; and a warning outputting portion 13. The present example is based on the same concept as examples above.

The rising/falling frequency detecting portion 11$d$ includes a trend line calculating portion 117 and a crossing frequency detecting portion 118.

Figure 15A:
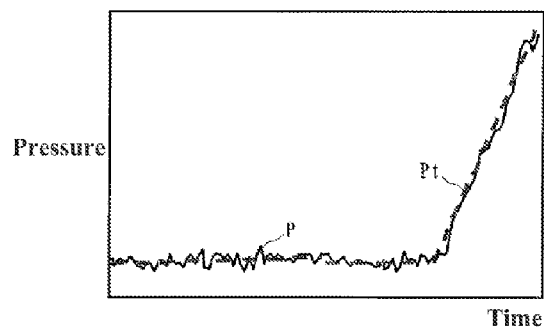
FIG. 15A-15B are waveform diagrams for explaining the operation of a pressure guiding tube blockage diagnosing device according to a further example according to the present invention.
Figure 15B:
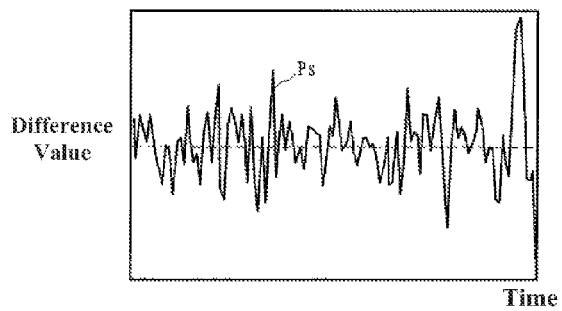

FIG. 15A and FIG. 15B are waveform diagrams for explaining the operation of the blockage diagnosing device according to the present example, where FIG. 15A is a diagram illustrating one example of the pressure values P measured by the pressure transmitting device 5 and the changes in the trend line Pt thereof, and FIG. 15B is a diagram illustrating the difference values Ps between the pressure values P and the trend line Pt. Note that while in FIG. 15A and FIG. 15B, the pressure values P and the difference values Ps are illustrated as continuous waveforms, in the present example the signals that are actually processed are pressure data that are sampled periodically and difference values Ps are also discrete data.

The trend line calculating portion 117 segments the time series of the pressure values P into a plurality of continuous intervals, and calculates the trend line Pt of the pressure values P for each interval. An example of a trend line Pt is, for example, a least-squares approximation line of the time series of the pressure values P.

Following this, the crossing frequency detecting portion 118 counts, for each interval, the number of times that the pressure value P crosses the trend line Pt in the applicable detection interval. Specifically, the crossing frequency detecting portion 118 may calculate the difference values Ps between the pressure values P and the trend line Pt, as illustrated in FIG. 15B, to count, for each interval, the number of zero crossings of the difference values Ps. The number of zero crossings serves as the rising/falling frequency for the fluctuation of the pressure.

As with the above examples, the ratio calculating portion 120 of the evaluating portion 12 calculates, for each interval, a ratio wherein the number of zero crossings, counted by the crossing frequency detecting portion 118, is divided by the number of samples in an interval. The operation of the comparing portion 121 and the warning outputting portion 13 are identical to those in the examples above.

Figure 16:
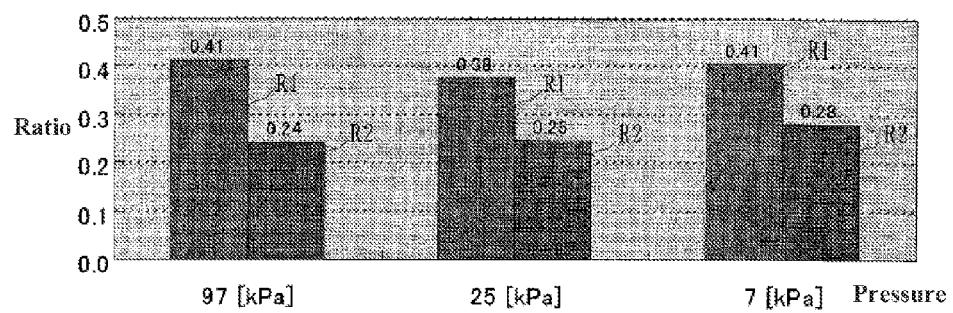
FIG. 16 is a diagram for explaining the effects of a pressure guiding tube blockage diagnosing device according to the further example of the present invention.

FIG. 16 is a diagram for explaining the effect of the present example, a diagram illustrating the ratio of the zero crossing frequency to the number of samples in three pressure states. FIG. 16 is based on pressure data calculated in the same manner as in the case in FIG. 5. It can be understood from FIG. 16 that the ratio is different during the proper operations and during the improper operations, and that the difference is adequate for diagnosing a pressure guiding tube blockage. In the example in FIG. 16, it can be seen that setting the threshold value to about 0.3 makes it possible to discriminate between the case wherein the pressure guiding tube is normal and the case wherein the pressure guiding tube is blocked. Moreover, it can be seen that there is no large change in the state of the ratio regardless of whether the pressure being measured is 97 kPa, 25 kPa, or 7 kPa, and thus there is no need to change the threshold value even if there is a large change in the pressure being measured.

As described above, the same effect as in the examples above can be obtained through the present example. Additionally, in the present example, the calculations follow well the fluctuation in the pressure values P, but have additional calculating overhead relative to the above example.

While in the examples above, for each interval, the number of crossings of the pressure value P for a detecting interval and a reference value calculated during the previous reference value calculating interval were counted, the reference value calculating interval and the detecting interval may be identical. That is, the number of times the pressure value P crosses the reference value during a detecting interval may be counted after calculating the reference value for the pressure value P during that detecting interval. In the present example as well, the structure of the pressure guiding tube blockage diagnosing device is identical to that in the above example, and thus the codes in FIG. 3 will be used in the explanation.

Figure 17:
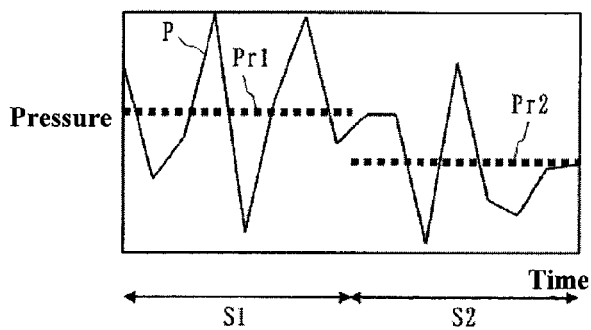
FIG. 17 is a waveform diagram for explaining the operation of a pressure guiding tube blockage diagnosing device according to a yet further example of the present invention.

FIG. 17 is a waveform diagram for explaining the operation of the blockage diagnosing device according to the present example, a diagram illustrating one example of the changes in the pressure value P measured by the pressure transmitting device 5. Note that while in FIG. 17 the waveform is illustrated as the pressure values P being connected, the signal that is actually processed in the present example is pressure data that are sampled periodically.

The reference value calculating portion 110 in the present example segments the time series of the pressure values P into a plurality of continuous intervals S1, S2, . . . , and calculates the reference value Pr of the pressure values P for each interval. Pr1 and Pr2, illustrated in FIG. 17, are the respective reference values calculated in intervals S1 and S2. As with the above examples, an average value or central value of the pressure values P is used as the reference value.

Following this, the crossing frequency detecting portion 111 counts, for each interval, the number of times that the pressure value P crosses the reference value Pr, calculated during that interval, in the applicable detection interval. That is, if the applicable detection interval is S2, then the number of tithes that the pressure value P in the interval S2 crosses the reference value Pr2 is counted. The crossing frequency is the pressure fluctuation rising/falling frequency. The operation of the evaluating portion 12 and the warning outputting portion 13 are identical to those in the examples above.

While the effects of the present example are based on those in the above examples, the crossing frequency cannot be calculated because the reference value is not certain prior to all of the samples of the interval being in place. Consequently, when compared to the examples above, this is somewhat less suitable for an on-line application.

Figure 18:
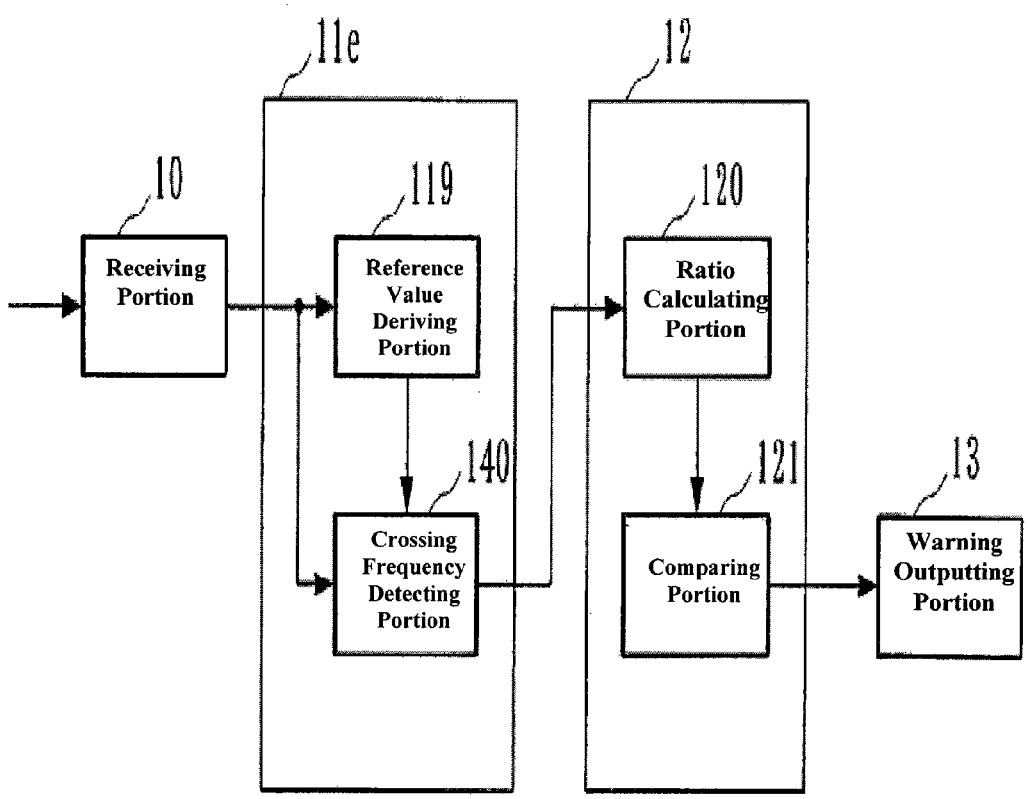
FIG. 18 is a block diagram illustrating the structure of a pressure guiding tube blockage diagnosing device according to the yet further example according to the present invention.

While in the above example an average value or a central value was used as the reference value for the pressure value P, instead, the first pressure value P during the detecting interval may be used as the reference value. FIG. 18 is a block diagram illustrating the structure of a pressure guiding tube blockage diagnosing device according to a yet further example according to the present invention, where structures identical to those in FIG. 3 are assigned identical codes. The blockage diagnosing device according to the present example is structured from: a receiving portion 10; a rising/falling frequency detecting portion 11e; an evaluating portion 12; and a warning outputting portion 13.

The rising/falling frequency detecting portion 11e comprises a reference value deriving portion 119 and a crossing frequency detecting portion 140.

The reference value deriving portion 119 of the rising/falling frequency detecting portion 11e segments the time series of the pressure values P into a plurality of continuous intervals, and uses as the reference value for each interval the initial pressure value P of that interval.

Following this, the crossing frequency detecting portion 140 of the rising/failing frequency detecting portion 11 counts, for each interval, the number of times that the reference value of that interval is crossed by the pressure value P during the applicable detection interval. The crossing frequency is the pressure fluctuation rising/falling frequency.

The operation of the evaluating portion 12 and the warning outputting portion 13 are identical to those in the above examples.

Although the point in the present example that the crossing frequency is counted in real time is the same as in the above examples, the calculation overhead is reduced to the extent that the calculation of the average value or central value is unnecessary, so the device is simple as well. Because the initial pressure value during the detecting interval is used as the reference value, instead of the average value or the central value, the calculations during the first interval are somewhat rougher; however, if a sufficiently large number of intervals is taken and an average value of the crossing frequencies in the individual intervals is calculated, then a significant diagnosing effect can be obtained by applying the average value of the crossing frequencies to the evaluating portion 12. However, the time required for the diagnosis is longer when using the average value of the crossing frequencies of a plurality of intervals.

Note that in the above examples ratios were calculated by dividing the rising/falling frequencies for the fluctuations by the number of samples within a single interval, and these ratios were compared to a threshold values, there is no limitation thereto, and, of course, the rising/falling frequencies can be compared to threshold values directly instead.

Figure 19:
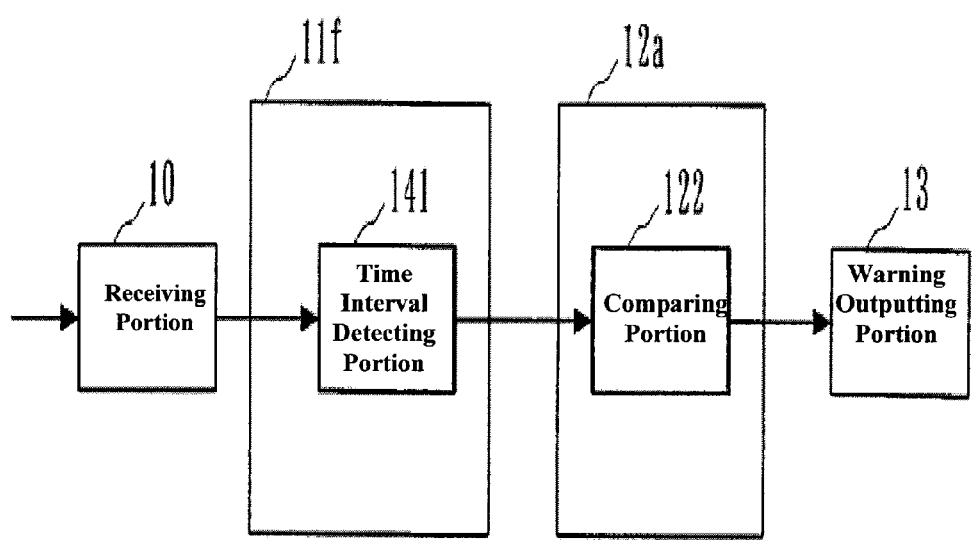
FIG. 19 is a block diagram illustrating the structure of a pressure guiding tube blockage diagnosing device according to an example according to the present invention.
Figure 20:
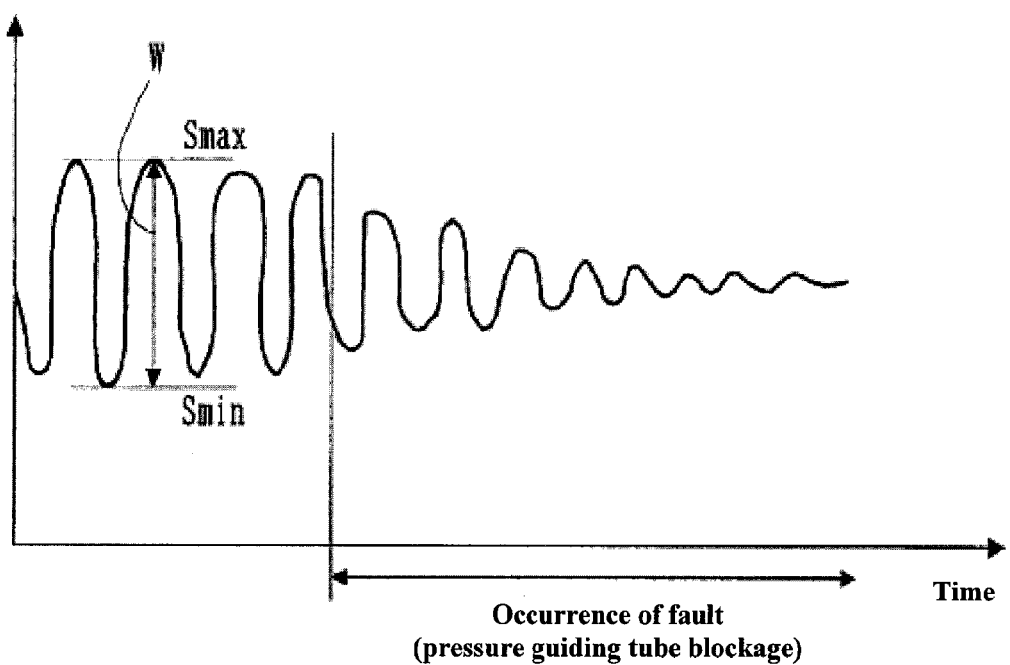
FIG. 20 is a diagram for explaining a conventional pressure guiding tube blockage diagnosing device.

An example of the present invention is explained next. FIG. 19 is a block diagram illustrating the structure of a pressure guiding tube blockage diagnosing device according to an example according to the present invention, where structures identical to those in FIG. 3 are assigned identical codes. The blockage diagnosing device according to the present example is structured from a receiving portion 10; a rising/falling frequency detecting portion 11f; an evaluating portion 12a; and a warning outputting portion 13.

In the present example, the time interval between a local maximum and a local minimum of the pressure value P is detected as information corresponding to the rising/falling, frequency of the fluctuation in pressure. The rising/falling frequency detecting portion 11f comprises a time interval detecting portion 141. The evaluating portion 12a includes a comparing portion 122.

The time interval detecting portion 141 segments the time series of the pressure values P into a plurality of continuous intervals, and detects the time intervals of the local maxima and local minima for the pressure values P for each interval.

For example, as is clear from the example in FIG. 4, a plurality of local maxima and local minima appear in the pressure value P during a single interval, there will also be a plurality of time intervals detected during a single interval. Consequently, the time interval that is actually calculated by the time interval detecting portion 141 is an average value of the plurality of time intervals.

The comparing portion 122 of the evaluating portion 12a compares the time interval calculated by the time interval detecting portion 141 to a threshold value that has been set in advance, and if the time interval is continuously higher than the threshold value, then the evaluation is that a blockage has occurred in the pressure guiding tubes 3 and 4. Specifically, when the time interval is greater than the threshold value a specific number of times in a row, or if the average value for the time intervals for a specific number of intervals is greater than the threshold value, then the comparing portion 122 may determine that a blockage has occurred in the pressure guiding tubes 3 and 4.

The operation of the warning outputting portion 13 is identical to those in the above example. As described above, the same effect as in the above example can be obtained through the present example.

Note that, in all of the examples, at least the rising/falling frequency detecting portions 11, 11a, 11b, 11c, 11d, 11e, and 11f, and the evaluating portions 12 and 12a, may be achieved through a computer that is provided with a CPU, a memory, a storage device, and an interface, and through a program that controls these hardware resources. The CPU executes the processes explained in all of the examples of embodiment, in accordance with a program that is stored in the memory.

The present invention can be applied to a technology for pressure guiding tube blockage diagnosing technologies.

What is claimed is:

1. A pressure guiding tube blockage diagnosing device, comprising:
   a pressure detector detecting, through a pressure guiding tube, a pressure to be measured, wherein there are fluctuations in the pressure;
   a fluctuation speed detector detecting a speed of the fluctuations based on a pressure value detected by the pressure detector; and
   an evaluator evaluating a blocked state of the pressure guiding tube based on the speed of the fluctuations, wherein
   the fluctuation speed detector is provided with a rising/falling frequency detector segmenting a time series of the pressure values detected by the pressure detector into a plurality of intervals and detecting, for each interval, the rising/falling frequency of the fluctuation, or data corresponding to the rising/falling movement frequency, as information indicating the speed of the fluctuations, and
   the evaluator is provided with a comparator evaluating the state of blockage of the pressure guiding tubes through comparing, to a specific threshold value, the rising/falling frequency of the fluctuation or data corresponding to the rising/falling frequency.

2. The pressure guiding tube blockage diagnosing device as set forth in claim 1, wherein
   the rising/falling frequency detector comprises:
   a reference value calculator calculating, for each interval, a reference value for the pressure detected by the pressure detector; and
   a crossing frequency counter counting, as the rising/falling frequency for each interval, the number of times during the applicable detecting interval that the pressure crosses the reference value calculated during the immediately preceding interval.

3. The pressure guiding tube blockage diagnosing device as set forth in claim 2, wherein
the reference value is an average value or central value of the pressure value.

4. The pressure guiding tube blockage diagnosing device as set forth in claim 1, wherein
the rising/falling frequency detector comprises:
a difference value detector detecting a difference value between the pressure value detected by the pressure detector and a pressure value of a specific time interval earlier; and
a crossing frequency detector counting, as the rising/falling frequency for each interval, the number of times during the applicable detecting interval that the difference value crosses zero.

5. The pressure guiding tube blockage diagnosing device as set forth in claim 1, wherein
the rising/falling frequency detector comprises:
a local maximum/local minimum detector counting, as the rising/falling frequency of each interval, the number of local maxima and local minima of the pressure values detected by the pressure detector.

6. The pressure guiding tube blockage diagnosing device as set forth in claim 1, wherein
the rising/falling frequency detector comprises:
a moving average value calculator calculating a moving average value of the pressure values detected by the pressure detector; and
a crossing frequency detector counting, as the rising/falling frequency for each interval, the number of times during the applicable detecting interval that the pressure value crosses the moving average value.

7. The pressure guiding tube blockage diagnosing device as set forth in claim 1, wherein
the rising/falling frequency detector comprises:
a rate-of-change limit processor for performing a rate-of-change limit process on the pressure value detected by the pressure detector;
a second-order lag processor performing second-order lag processing on the pressure values after the rate-of-change limit processing; and
a crossing frequency detector counting, as the rising/falling frequency during each interval, the number of times during the applicable detecting interval that the pressure value crosses the output value of the second-order lag processor.

8. The pressure guiding tube blockage diagnosing device as set forth in claim 1, wherein
the rising/falling frequency detector comprises:
a trend line calculator calculating a trend line of the pressure values detected by the pressure detector; and
a crossing frequency detector counting, as the rising/falling frequency for each interval, the number of times during the applicable detecting interval that the pressure value crosses the trend line.

9. The pressure guiding tube blockage diagnosing device as set forth in claim 1, wherein
the rising/falling frequency detector comprises:
a reference value deriver using, as the reference value in each interval, the initial pressure value for each interval; and
a crossing frequency detector counting, as the rising/falling frequency for each interval, the number of times in the applicable detecting interval that the pressure value crosses the reference value.

10. The pressure guiding tube blockage diagnosing device as set forth in claim 1, wherein
the comparator evaluates that a blockage has occurred in the pressure guiding tube if the rising/falling frequency of the fluctuation is continuously below the threshold value.

11. The pressure guiding tube blockage diagnosing device as set forth in claim 1, wherein
the evaluator is further provided with ratio calculator calculating, for each individual interval, the ratio of the rising/falling frequency of the fluctuation divided by the number of samples in the interval, and wherein
the comparator, rather than comparing the rising/falling frequency of the fluctuation to the threshold value, compares the ratio to the threshold value, and evaluates that a blockage has occurred in the pressure guiding tube if the ratio is continuously below the threshold value.

12. The pressure guiding tube blockage diagnosing device as set forth in claim 1, wherein
the rising/falling frequency detector comprises:
a time interval detector detecting, as information corresponding to the rising/falling frequency of each interval, the time intervals between local maxima and local minima of the pressure values detected by the pressure detector.

13. The pressure guiding tube blockage diagnosing device as set forth in claim 12, wherein
the comparator evaluates that a blockage has occurred in the pressure guiding tube if the time interval is continuously above the threshold value.

14. A pressure guiding tube blockage diagnosing method, comprising:
a pressure detecting step of detecting, through a pressure guiding tube, a pressure to be measured, wherein there are fluctuations in the pressure;
a fluctuation speed detecting step of detecting a speed of the fluctuations based on a pressure value detected by the pressure detecting step; and
an evaluating step of evaluating a blocked state of the pressure guiding tube based on the speed of the fluctuations, wherein
the fluctuation speed detecting step further comprises:
a rising/falling frequency detecting step comprising:
a segmenting step of segmenting a time series of the pressure values detected by the pressure detecting step into a plurality of intervals; and
a detecting step of detecting, for each interval, the rising/falling frequency of the fluctuation, or data corresponding to the rising/falling movement frequency, as information indicating the speed of the fluctuations, and wherein
the evaluating step further comprises:
evaluating the state of blockage of the pressure guiding tubes through comparing, to a specific threshold value, the rising/falling frequency of the fluctuation or data corresponding to the rising/falling frequency.

* * * * *